(12) United States Patent
Kaufmann et al.

(10) Patent No.: US 8,535,940 B2
(45) Date of Patent: Sep. 17, 2013

(54) CELL GROWTH

(75) Inventors: Hitto Kaufmann, Ulm (DE); Lore Florin, Biberach (DE); Eric Becker, Hochdorf (DE)

(73) Assignee: Boehringer Ingelheim Pharma GmbH & Co. KG, Ingelheim Am Rhein (DE)

( * ) Notice: Subject to any disclaimer, the term of this patent is extended or adjusted under 35 U.S.C. 154(b) by 553 days.

(21) Appl. No.: 12/524,219

(22) PCT Filed: Jan. 22, 2008

(86) PCT No.: PCT/EP2008/050699
§ 371 (c)(1),
(2), (4) Date: Oct. 7, 2009

(87) PCT Pub. No.: WO2008/090148
PCT Pub. Date: Jul. 31, 2008

(65) Prior Publication Data
US 2010/0086967 A1  Apr. 8, 2010

(30) Foreign Application Priority Data
Jan. 24, 2007 (EP) ..................... 07101070

(51) Int. Cl.
*A61K 39/395* (2006.01)
*C12N 5/10* (2006.01)
*A61P 35/00* (2006.01)
*C12P 21/00* (2006.01)

(52) U.S. Cl.
USPC .... 435/325; 435/320.1; 435/69.6; 530/387.3; 530/387.9; 530/391.3

(58) Field of Classification Search
None
See application file for complete search history.

(56) References Cited

U.S. PATENT DOCUMENTS
5,776,746 A  7/1998 Denney, Jr.
6,221,675 B1  4/2001 Hauptmann et al.
2003/0219871 A1  11/2003 Enekel et al.

FOREIGN PATENT DOCUMENTS
EP  0393438 A2  10/1990
EP  1 348 758 A1  10/2003
EP  1953222 A1  8/2008

OTHER PUBLICATIONS

Dyring et al (Stable, recombinant expression of human insulin-like growth factor binding protein-1 (hIGFBP-1) in Chinese hamster ovary (CHO) cells Cytotechnology vol. 24, No. 3, 193-200).*
International Search Report for PCT/EP2008/050699 mailed on Jul. 21, 2008.
Meents, Heiko, et al; Impact of Coexpression and Coamplification of sICAM and Antiapoptosis Determinants bcl-21 bcl-$x_L$ on Productivity, Cell Survival, and Mitochondria Number in CHO-DG44 Grown in Suspension and Serum-Free Media; Biotechnology and Bioengineering (2002) vol. 80, No. 6 pp. 706-716.
Meents, Heiko, et al; Amplified Dicistronic Expression Units Mediate Apoptosis Protection in CHO-DG44 Cells Adapted for Growth in Serum-Free Media, Impact on Mitochondria Copy Number; Animal Cell Technology Meets Genomics. Proceedings of the Esact Meeting (2003) vol. 2 pp. 115-12.
5,843,791, Dec. 1, 1998, Hauptmann, (withdrawn).
Chrast, Roman et al. "Linearization and purification of BAC DNA for the development of transgenic mice" Transgenic Research, 8: 147-150 (1999).
Eastman, Helen B., et al. "Stimulation of dihydrofolate reductase promoter activity by anitmetabolic drugs" Proc. Natl. Acad. Sci., vol. 88, 8572-8576, Oct. 1991.
International Search Report for PCT/EP2009/059400 mailed Oct. 6, 2009.
Lee, Moon Sue, et al. "Proteome Analysis of Antibody-Expressing CHO Cells in Response to Hyperosmotic Pressure" Biotechnology Progress, vol. 19, 1734-1741 (2003).
Wurm, Florian M, et al. "Gene transfer and gene amplification in mammalian cells" S.C. Makrides (Ed.) Elsevier Science B.V., Ch 7, pp. 309-335 (2003).

* cited by examiner

*Primary Examiner* — Kagnew H Gebreyesus
(74) *Attorney, Agent, or Firm* — Michael P. Morris; Edouard G. Lebel; Usha R. Patel

(57) ABSTRACT

The invention concerns the field of cell culture technology. It concerns a method of improving cell growth, especially the growth of biopharmaceutical producer host cells. The invention further concerns a method of producing proteins using the cells generated by the described method.

3 Claims, 2 Drawing Sheets

(a)

(b)

CELL GROWTH

This application is the national phase entry under 35 U.S.C. §371 of International Application No. PCT/EP2008/050699, filed Jan. 22, 2008, which claims priority to European Patent Application No. 07101070.6, filed Jan. 24, 2007, which are hereby incorporated by reference in their entireties.

BACKGROUND OF THE INVENTION

Technical Field

The invention concerns the field of cell culture technology. It concerns a method of improving cell growth as well as a method for generating a production host cell line. The invention further concerns a method of producing proteins using the cells generated by the described method.

Background

The market for biopharmaceuticals for use in human therapy continues to grow at a high rate with 270 new biopharmaceuticals being evaluated in clinical studies and estimated sales of 30 billions in 2003 (Werner 2004). Currently, an increasing number of biopharmaceuticals is produced from mammalian cells due to their ability to correctly process and modify human proteins. Successful and high yield production of biopharmaceuticals from mammalian cells is thus crucial and depends on the characteristics of the recombinant monoclonal cell line used in the process.

In biopharmaceutical production processes, yield is determined by two factors: the specific productivity ($P_{spec}$) of the host cell and the IVC, the integral of viable cells over time which produce the desired protein. This correlation is expressed by the following formula: $Y = P_{spec} * IVC$. Standard approaches to improve product yield therefore can be to increase either the production capacity of the host cell or viable cell densities in the bioreactor. One method to obtain higher IVCs is to improve the growth characteristics of cells, that means to generate cells which grow faster and to higher maximal cell densities.

Enhanced cell growth has a profound impact on multiple aspects of the biopharmaceutical production process:
 Shorter generation times of cells, which results in prolonged time lines in cell line development;
 Higher efficiency after single-cell cloning and slower growth thereafter;
 Shorter timeframes during scale-up, especially in the case of inocculum for a large-scale bioreactor;
 Higher product yield per fermentation time due to the proportional correlation between IVC and product yield. Conversely, a low IVCs cause lower yields and/or longer fermentation times.

The enzyme dihydrofolate reductase (DHFR) is one of the key enzymes of nucleotide synthesis. It catalyzes the reduction of di-hydrofolat to tetra-hydrofolat, a universal transmitter of C1-units in the synthesis of purin building blocks and of other metabolic pathways.

In biopharmaceutical industry and in academic research DHFR is widely used as a selection and amplification marker for the selective growth of stable transfected cell lines. Thereby, the expression of DHFR is functionally linked to the expression of a gene of interest (GOI), e.g. the expression cassette for a product gene. Thus, GOI-expressing cells are enriched for indirectly via the resistance conferred to by DHFR under selective conditions. This functional coupling is usually mediated/constituted by the bi-cistronic expression of both genes or at least their co-location on the same plasmid.

Since DHFR is a non-dominant marker, this system is mostly used in cells which lack endogenous DHFR activity. Hence, when in the 1980's dhfr-negative chinese hamster ovary (CHO) cells, CHO-DG44 and CHO-DUKX (B11), became available, they rapidly advanced to the host cell system of choice and are today the worldwide most frequently used mammalian production platform in the biopharmaceutical industry.

The DHFR enzyme is one of the key enzymes in the biosynthesis pathway of purines. Cells which lack DHFR are therefore not viable unless DHFR-deficiency is compensated by the addition of the nucleotide precursors hypoxanthine and thymidine (HT) into the culture medium.

Surprisingly it is shown in the present invention that even in HT supplemented medium, dhfr-deficient CHO cells grow markedly slower and markedly less dense if compared to parental CHO wild type cells (FIG. 1).

This reduced growth capacity, as shown in the present invention for dhfr-negative cells (such as the CHO-DG44 cells) or in cells with a very low endogenous dhfr-level, has a negative impact on multiple aspects of the biopharmaceutical production process:
 Prolonged generation times of cells, which results in prolonged time lines in cell line development
 Lower efficiency after single cell cloning and slower growth thereafter
 Longer timeframes during scale up, especially in the case of inocculum for a production fermenter at large scale
 Lower product yield per fermenter run.

These disadvantages are directly connected to the growth characteristics of the production cell (e.g. CHO-DG44 or DUKX (B11)). They occur for example, when these cells are used in connection with the following selection and amplification systems: glutamine synthetase (GS) system, neomycin, puromycin, bleomycin and others.

To compensate for growth deficiencies in cells, especially biopharmaceutical production cell lines, most efforts have been directed to improving the culture medium by adding growth supplements such as carbohydrates, nucleosides, trace elements, protein hydrolysates, plant extracts etc. . . . . It is possible, for example, to slightly increase the growth of dhfr-negative cells by the addition of protein hydrolysate into the culture medium, but they do not reach the growth level of wild type cells.

Therefore, there exists a strong need to improve the growth characteristics of producer host cells, especially those with low or no endogenous DHFR expression such as CHO-DG44. Additionally, enhanced cell growth and thus higher IVC's during fermentation are clearly advantageous wherever high biomasses are required, e.g. in order to get high product yield in short-term fermentations, to harvest high cell numbers for isolation, purification or characterision of intracellular or cell-bound components or to shorten the timelines for cell line generation, single-cell cloning and culture up-scaling.

SUMMARY OF THE INVENTION

The overall goal of the present invention is the improvement of cell growth during biopharmaceutical production processes in order to increase cell density and thus product yield.

This goal is achieved in the present invention by the introduction of a DHFR expression cassette into production cells. The present invention thus surprisingly shows that enhanced cell growth is obtained by heterologous expression of the enzyme dihydrofolate reductase (DHFR).

In the present invention the DHFR gene does not serve the usual purpose as selection marker for another gene, a gene of interest (GOI), but it exerts an independent function of increasing cell growth. In this setting, the DHFR gene is not functionally linked/coupled to one or several other expression cassettes. It thus can be on the same plasmid as the GOI or it may be expressed from a separate vector. If both genes are on separate vector constructs, the plasmids can be co-transfected or they can be sequentially brought into the cell.

In the present invention it has surprisingly been shown for the first time, that dhfr-deficiency leads to a reduced cell growth. It could furthermore be shown, that re-introduction of DHFR can solve this problem.

The re-introduction of a DHFR-transgene does not only lead to a reduction in the doubling time, but also the IVC is increased to wild type levels or even beyond (FIG. 1). This growth enhancing effect can not only be observed in two different DG44 cell lines, but also applies for CHO DUKX B11 cells transfected with a functional DHFR gene. Transfection with expression constructs harbouring puromycin or neomycin restistance cassettes, however, do not lead to changes in cellular growth characteristics. This indicates, that the growth enhancement is not due to selection and/or cultivation of stable transfectants, but is caused by the re-establishment of functional DHFR expression in dhfr-negative CHO cells.

Furthermore, heterologous expression of DHFR displays a gene-dosage effect, meaning that the growth characteristics of the stable cell subclones increase proportionally to the expression of active DHFR protein (FIG. 2a,b).

Notably, this effect seems not to apply for cell lines in which the DHFR gene has been amplified by MTX treatment (Gu et al, 1992, Pendse et al, 1992). This might either point to a threshold in the levels of active DHFR above which no further growth enhancement is obtained, or to a compensatory effect of the inhibitor MTX, that in high concentrations exceeding the molecular concentration of DHFR enzyme will outbalance the amplification of the dhfr gene, leading to a net reduction in DHFR activity and thus reduced cell growth.

The present invention addresses the general problem of enhancing the growth of cell lines, especially production cell lines with low or no endogenous DHFR expression. In these cells, the growth characteristics can be improved significantly by the heterologous expression of DHFR.

The heterologous expression of DHFR in dhfr-deficient host cells has the additional advantages of resulting in a reduced time frame during the expansion and inocculum process of fermentation, in an increased IVC, e.g. in production processes, and thus in a higher product yield.

The host cells and methods of the invention are furthermore applicable in the biopharmaceutical production, especially when using the host cell systems based on CHO-DG44 or CHO-DUKX-B11. Moreover, they can be used wherever high yields of recombinant protein are desired, e.g. for purification/structural analysis in research, or when large cell biomasses are required, e.g. for isolation/investigation of cellular components such as nucleic acids or proteins.

In a preferred embodiment of the present invention the host cells and methods of the present invention may be combined with selection system(s) such as the glutamine synthetase- (GS-) system, adenosine deaminase (ADA), cytosine deaminase (CDA), puromycin, neomycin, bleomycin etc. . . . . This can result in higher growth rates and higher cell densities during the fermentation process.

The present invention is not obvious from the prior art.

CHO cells were established for the study of somatic cell genetics in 1957 (PUCK, 1957). By mutagenesis of the original K1 cell line, Urlaub and Chasin developed DHFR-deficient "CHO DG44" cells (Urlaub and Chasin, 1980) which exhibited a homozygous deletion of the chromosomal dhfr-locus (Urlaub et al., 1983). The growth properties of this newly established cell line were not investigated by the authors.

CHO DG44 cells quickly became the method of choice for transfections which employed the use of expression vectors carrying a functional dhfr gene together with an expression cassette for the gene of interest (GOI). DHFR is a non-dominant selection marker and hence is best used in cells lacking DHFR. However, it has been shown to be also applicable in host cells containing endogenous DHFR activity, e.g. by selecting with a second dominant marker (Kaufman et al., 1986), or mutant or bacterial dhfr genes (Simonsen and Levinson, 1983; Asselbergs and Widmer, 1995).

Under selective conditions, heterologous DHFR expression enables transfected cells to survive and proliferate. It has not been shown, however, that DHFR confers a growth advantage independent of its function as a selection marker and under non-selective conditions.

The dhfr gene belongs to the amplification markers, allowing the co-amplification of foreign genes after treatment with the folat analog methothrexat (MTX) (Schimke et al., 1978; Alt et al., 1978; Pallavicini et al., 1990). There is conclusive evidence, that co-amplification of a GOI together with dhfr is not dependent on whether both genes are contained on the same plasmid (Kaufman and Sharp, 1982). Consequently, expression strategies for recombinant antibody production have been reported where either both antibody chains are located on the same DNA plasmid together with the dhfr gene (Page and Sydenham, 1991), in which only one chain is functionally coupled with a dhfr expression cassette (Fouser et al., 1992) or where dhfr is encoded on a separate, co-integrating plasmid (Wurm and Jordan, 2003).

There are reports indicating that structural linkage of the dhfr gene and the GOI on the same DNA plasmid is not a pre-requisite for co-amplification since different co-transfected DNA constructs tend to co-integrate into adjacent chromosomal loci (Wurm, F. M. and Jordan, M. 2003. Gene Transfer and Gene Amplification in Mammalian Cells. In: Gene Transfer and Expression in Mammalian Cells, ed. S. C. Makrides Elsevier Science B. V., 309-335). It is important to note, that also in this setting, DHFR serves as a selection and/or amplification marker for the foreign GOI which constitutes a functional linkage despite structural separation.

In contrast, the present invention is based on the observation that heterologous DHFR, besides its well-known function as selection-/amplification marker for a GOI, exerts a completely independent function in improving cell growth.

Interestingly, there are numerous reports linking high DHFR expression with reduced cell growth, thereby opposing the desirable effect of heterologous gene amplification. Previous studies with *Escherichia coli* and *Saccharomyces cerevisiae* demonstrated that amplified dhfr gene copy numbers were accompanied by a decrease in the specific growth rate. (Bailey et al, 1986). Gu et al. showed reduced growth rates in beta-galactosidase expressing CHO-DG44 cells after dhfr-gene amplification by MTX treatment (Gu et al, 1992). Similar data were presented by Pendse et al. using a viral transgene coupled to DHFR (Pendse et al, 1992). Notably, both studies did not include cells expressing DHFR alone which prevents to conclude about the individual contribution of the multiple transgenes used. Importantly, they only compared the growth characteristics of dhfr-expressing amplified and un-amplified cells. Untransfected CHO-DG44 were not included. Snapka et al. demonstrated a reduction in cell growth with increasing dhfr gene copy numbers in NIH3T3-derived cells (Snapka et al, 1997). Interestingly and in contrast to their suggested mechanism, they also showed another adherent cell line which grew to higher cell densities after MTX-mediated dhfr amplification. They attributed this effect to reduced contact inhibition—which is not relevant for cells growing in suspension.

Taken together, in the present invention it is demonstrated for the first time, that heterologous expression of DHFR leads to an improvement of growth characteristics in CHO cells, especially CHO DG44 and CHO DUXX-(B11) cells. This function of DHFR might also be used to enhance cellular growth rates in other dhfr-negative or dhfr-reduced cell lines.

(b) Relative IVC's of the cells shown in (a). The integral cell area at day 5 was calculated and plotted relative to WT levels which were set 100%. Error bars represent the standard deviations of at least three independent experiments.

(c) Growth characteristics during long-term cultivation. Cells were maintained at cell densities between 0.3-2.5 E06 cells/ml and splitted every 2-3 days over 8 passages. Growth rate (black bars) and doubling time (shaded bars) were calculated and plotted for wild type CHO, DG44 and dhfr-transfected DG44 cells.

Figure 2:
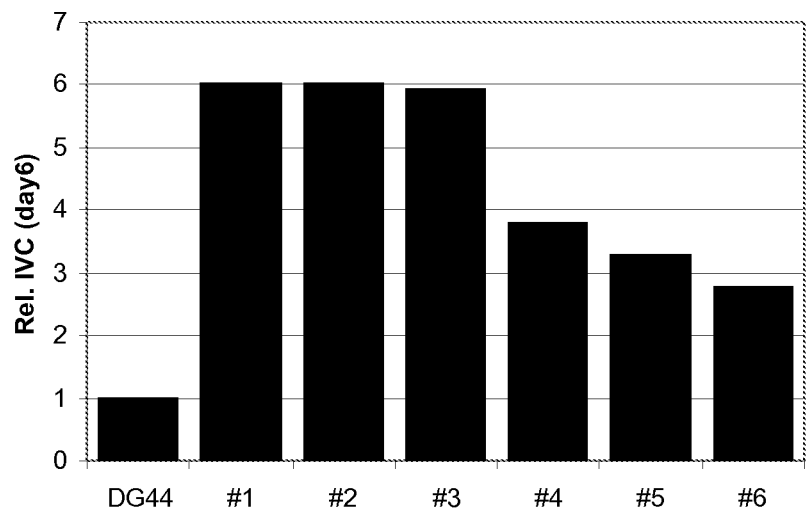
Figure 2:
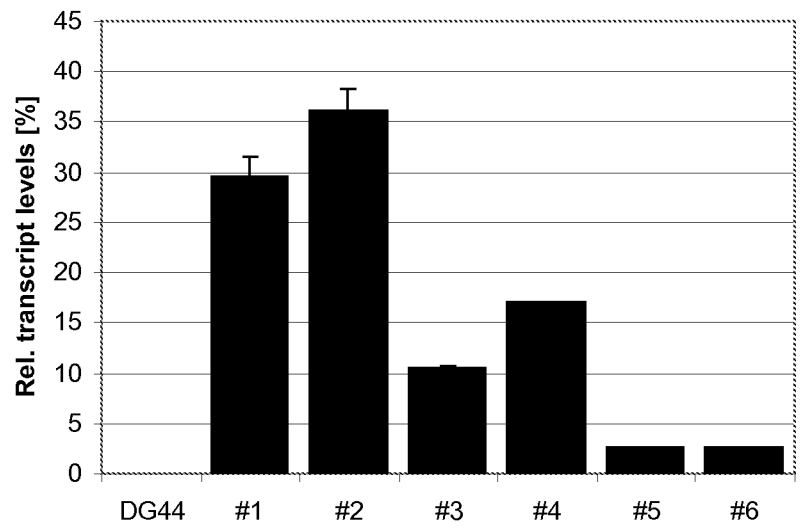

FIG. 2: DOSAGE-DEPENDENT GROWTH ENHANCEMENT (a) Enhanced cell growth in DHFR-transfected subclones. Six stable DHFR-transfected cell pools were generated by heterologous introduction of a DHFR expression cassette into CHO DG44 cells. From these, clonal cell populations were obtained by FACS-based single-cell cloning and subjected to fed-batch fermentation. The IVC of the DHFR clones at day 6 was calculated and plotted relative to the IVC of the parental DG44 cell line which was set to 1.

(b) Relative DHFR expression. Total RNA was isolated from the above mentioned cells and quantitative real-time PCR was performed to determine DHFR-specific mRNA transcripts. Beta-tubulin was used for normalization.

DETAILED DESCRIPTION OF THE INVENTION

Definitions

The general embodiments "comprising" or "comprised" encompass the more specific embodiment "consisting of". Furthermore, singular and plural forms are not used in a limiting way.

Terms used in the course of this present invention have the following meaning.

The term "DHFR-deficient" means the same as "DHFR-negative". This describes cells not functionally expressing the DHFR enzyme. This can be caused by either homozygous deletion or mutation of the DHFR gene.

The term "DHFR-reduced" means cells with low endogenous DHFR levels, e.g. cells heterozygous for the DHFR gene.

The term "integral of viable cell concentration over time" (IVC) means the area below the growth curve of a cell plotted over time and is a commonly used parameter to describe the growth performance of cells, e.g. in production processes which run over several days to weeks.

The term "cell culture" means multiple cells cultivated in one container under conditions suitable for the growth of the cells.

"Host cells" in the meaning of the present invention are cells such as hamster cells, preferably BHK21, BHK TK⁻, CHO, CHO-K1, CHO-DUKX, CHO-DUKX B1, and CHO-DG44 cells or the derivatives/progenies of any of such cell line. Particularly preferred are CHO-DG44, CHO-DUKX, CHO-K1 and BHK21, and even more preferred CHO-DG44 and CHO-DUKX cells. In a further embodiment of the present invention host cells also mean murine myeloma cells, preferably NS0 and Sp2/0 cells or the derivatives/progenies of any of such cell line. Examples of murine and hamster cells which can be used in the meaning of this invention are also summarized in Table 1. However, derivatives/progenies of those cells, other mammalian cells, including but not limited to human, mice, rat, monkey, and rodent cell lines, or eukaryotic cells, including but not limited to yeast, insect and plant cells, can also be used in the meaning of this invention, particularly for the production of biopharmaceutical proteins.

TABLE 1

Hamster and murine production cell lines

| CELL LINE | ORDER NUMBER |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO-K1 | ATCC CCL-61 |
| CHO-DUKX (=CHO duk⁻, CHO/dhfr⁻) | ATCC CRL-9096 |
| CHO-DUKX B11 | ATCC CRL-9010 |
| CHO-DG44 | Urlaub et al., Cell 33[2], 405-412, 1983 |
| CHO Pro-5 | ATCC CRL-1781 |
| V79 | ATCC CCC-93 |
| B14AF28-G3 | ATCC CCL-14 |
| CHL | ECACC No. 87111906 |

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

The term "protein" is used interchangeably with amino acid residue sequences or polypeptide and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties.

The expression vector having a gene of interest encoding a protein of interest may also contain a selectable amplifiable marker gene.

The term "selective conditions" refers to conditions which do not allow for the growth or survival of cells which do not contain a corresponding selection marker. Selective conditions may be generated by using a medium containing additives such as antibiotics or lacking essential growth components.

The term "selectable marker" or "selection marker" is used for markers, which allow the growth/survival of cells under selective conditions. In the example of the selectable marker puromycin N-acetyl transferase (PAC) only cells containing the PAC gene will survive in selective media containing the antibiotic puromycin.

The term "amplifiable marker" or "amplification marker" is used for genes, which are amplified (e.g. doublicated, triplicated, multiplied) in the presence of a selective agent or upon treatment with a selective agent (e.g. methotrexat (MTX)) leading to an increase in the gene copy number of the marker (e.g. DHFR) and the surrounding DNA regions.

The "selectable amplifiable marker gene" usually encodes an enzyme which is required for growth of eukaryotic cells under those conditions. For example, the selectable amplifiable marker gene may encode DHFR which gene is amplified when a host cell transfected therewith is grown in the presence of the selective agent, methotrexate (MTX). The non-limited exemplary selectable genes in Table 3 are also amplifiable marker genes, which can be used to carry out the present invention. For a review of the selectable amplifiable marker genes listed in Table 3, see Kaufman, Methods in Enzymology, 185:537-566 (1990), incorporated by reference. Accordingly, host cells genetically modified according to any method described herein are encompassed by this invention, wherein the selectable amplifiable marker gene encodes for a polypeptide having the function of dihydrofolate reductase (DHFR), glutamine synthetase, CAD, adenosine deaminase, adenylate deaminase, UMP synthetase, IMP 5'-dehydrogenase, xanthine guanine phosphoribosyl transferase, HGPRTase, thymidine kinase, thymidylate synthetase, P glycoprotein 170, ribonucleotide reductase, asparagine synthetase, arginosuccinate synthetase, ornithine decarboxylase, HMG CoA reductase, acetylglucosaminyl transferase, threonyl-tRNA synthetase or $Na^+K^+$-ATPase.

A preferred selectable amplifiable marker gene is the gene encoding dihydrofolate reductase (DHFR) which is necessary for the biosynthesis of purines. Cells lacking the DHFR gene will not grow on medium lacking purines. The DHFR gene is therefore useful as a dominant selectable marker to select and amplify genes in such cells growing in medium lacking purines. The selection agent used in conjunction with a DHFR gene is methotrexate (MTX).

The term "DHFR gene" or "dhfr" means any nucleic acid encoding an active dihydrofolate reductase protein. This includes genomic DHFR sequences containing one or more introns, cDNA sequences or so called "minigenes", comprising DHFR regulatory sequences and coding sequences together with or without introns.

TABLE 3

Selectable amplifiable marker genes

| Selectable Amplifiable Marker Gene | Accession Number | Selection Agent |
|---|---|---|
| Dihydrofolate reductase | M19869 (hamster) E00236 (mouse) | Methotrexate (MTX) |
| Metallothionein | D10551 (hamster) M13003 (human) M11794 (rat) | Cadmium |
| CAD (Carbamoyl-phosphate synthetase:Aspartate transcarbamylase: Dihydroorotase) | M23652 (hamster) D78586 (human) | N-Phosphoacetyl-L-aspartate |
| Adenosine deaminase | K02567 (human) M10319 (mouse) | Xyl-A- or adenosine, 2'deoxycoformycin |
| AMP (adenylate) deaminase | D12775 (human) J02811 (rat) | Adenine, azaserine, coformycin |
| UMP synthase | J03626 (human) | 6-Azauridine, pyrazofuran |
| IMP 5'dehydrogenase | J04209 (hamster) J04208 (human) M33934 (mouse) | Mycophenolic acid |
| Xanthine-guanine phosphoribosyltransferase | X00221 (*E. coli*) | Mycophenolic acid with limiting xanthine |
| Mutant HGPRTase or mutant thymidine kinase | J00060 (hamster) M13542, K02581 (human) J00423, | Hypoxanthine, aminopterin, and thymidine (HAT) |

TABLE 3-continued

Selectable amplifiable marker genes

| Selectable Amplifiable Marker Gene | Accession Number | Selection Agent |
|---|---|---|
| Thymidylate synthetase | M68489 (mouse) M63983 (rat) M36160 (herpesvirus) D00596 (human) M13019 (mouse) L12138 (rat) | 5-Fluorodeoxyuridine |
| P-glycoprotein 170 (MDR1) | AF016535 (human) J03398 (mouse) | Multiple drugs, e.g. adriamycin, vincristine, colchicine |
| Ribonucleotide reductase | M124223, K02927 (mouse) | Aphidicolin |
| Glutamine synthetase | AF150961 (hamster) U09114, M60803 (mouse) M29579 (rat) | Methionine sulfoximine (MSX) |
| Asparagine synthetase | M27838 (hamster) M27396 (human) U38940 (mouse) U07202 (rat) | β-Aspartyl hydroxamate, Albizziin, 5'Azacytidine |
| Argininosuccinate synthetase | X01630 (human) M31690 (mouse) M26198 (bovine) | Canavanine |
| Ornithine decarboxylase | M34158 (human) J03733 (mouse) M16982 (rat) | α-Difluoromethylornithine |
| HMG-CoA reductase | L00183, M12705 (hamster) M11058 (human) | Compactin |
| N-Acetylglucosaminyl transferase | M55621 (human) | Tunicamycin |
| Threonyl-tRNA synthetase | M63180 (human) | Borrelidin |
| Na$^+$K$^+$-ATPase | J05096 (human) M14511 (rat) | Ouabain |

Suitable host cells for using a DHFR encoding gene as a selectable amplifiable marker are mammalian cells, preferably murine myeloma or hamster cells. More preferred are CHO-DUKX (ATCC CRL-9096) and CHO-DG44 (Urlaub et al., Cell 33[2], 405-412, 1983) cells which are deficient in DHFR activity. To extend the DHFR amplification method to other cell types, a mutant DHFR gene that encodes a protein with reduced sensitivity to methotrexate may be used in conjunction with host cells that contain normal numbers of an endogenous wild type DHFR gene (Simonson et al., 1983; Wigler et al., 1980; Haber et al., 1982).

The present invention is suitable to generate host cells for the production of biopharmaceutical polypeptides/proteins. The invention is particularly suitable for the high-yield expression of a large number of different genes of interest by cells showing an enhanced cell productivity.

"Gene of interest" (GOI), "selected sequence", or "product gene" have the same meaning herein and refer to a polynucleotide sequence of any length that encodes a product of interest or "protein of interest", also mentioned by the term "desired product". The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization or tagging. The selected sequence can encode a secreted, cytoplasmic, nuclear, membrane bound or cell surface polypeptide.

The "protein of interest" includes proteins, polypeptides, fragments thereof, peptides, all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use. Examples for a desired protein/polypeptide are also given below.

In the case of more complex molecules such as monoclonal antibodies the GOI encodes one or both of the two antibody chains.

The "product of interest" may also be an antisense RNA.

Proteins of interest or desired proteins are those mentioned above. Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors. The method according to the invention can also be advantageously used for production of antibodies or fragments thereof. Such fragments include e.g. Fab fragments (Fragment antigen-binding=Fab). Fab fragments consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

The protein of interest is preferably recovered from the culture medium as a secreted polypeptide, or it can be recovered from host cell lysates if expressed without a secretory signal. It is necessary to purify the protein of interest from other recombinant proteins and host cell proteins in a way that substantially homogenous preparations of the protein of interest are obtained. As a first step, cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a protein heterologous expressed by host cells, are well known in the art. Such methods are for example described by Harris and Angal, Protein Purification Methods, in Rickwood and Hames eds., The Practical Approach Series, IRL Press (1995) or Robert Scopes, Protein Purification, Springer-Verlag (1988), both incorporated by reference.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art are described in Huston et al. (1988, PNAS 16: 5879-5883).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins from the prior art can be found in Perisic et al. (1994, Structure 2: 1217-1226).

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins from the prior art can be found in Hu et al. (1996, Cancer Res. 56: 3055-61).

By triabody the skilled person means a: trivalent homotrimeric scFv derivative (Kortt et al. 1997 Protein Engineering 10: 423-433). ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures (Pack et al., 1993 Biotechnology 11: 1271-1277; Lovejoy et al. 1993 Science 259: 1288-1293; Pack et al., 1995 J. Mol. Biol. 246: 28-34).

By definition any sequences or genes introduced into a host cell are called "heterologous sequences" or "heterologous genes" or "transgenes" with respect to the host cell, even if the introduced sequence or gene is identical to an endogenous sequence or gene in the host cell.

Heterologous gene sequences can be introduced into a target cell by using an "expression vector", preferably an eukaryotic, and even more preferably a mammalian expression vector. Methods used to construct vectors are well known to a person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in Sambrook et al., 1989 and references cited therein. Vectors may include but are not limited to plasmid vectors, phagemids, cosmids, artificial/mini-chromosomes, or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

In a preferred embodiment the expression vector comprises at least one nucleic acid sequence which is a regulatory sequence necessary for transcription and translation of nucleotide sequences that encode for a peptide/polypeptide/protein of interest.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence as in the present examples. For example, mRNA transcribed from a selected sequence can be quantitated by Northern blot hybridization, ribonuclease RNA protection, in situ hybridization to cellular RNA or by PCR (see Sambrook et al., 1989; Ausubel et al., 1987 updated). Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis (see Sambrook et al., 1989; Ausubel et al., 1987 updated) or by homogeneous time-resolved fluorescence (HTRF) assays.

"Transfection" of eukaryotic host cells with a polynucleotide or expression vector, resulting in genetically modified cells or transgenic cells, can be performed by any method well known in the art and described, e.g., in Sambrook et al., 1989 or Ausubel et al., 1987 (updated). Transfection methods include but are not limited to liposome-mediated transfection, calcium phosphate co-precipitation, electroporation, polycation (such as DEAE-dextran)-mediated transfection, protoplast fusion, viral infections and microinjection. Preferably, the transfection is a stable transfection. The transfection method that provides optimal transfection frequency and expression of the heterologous genes in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell.

The practice of the present invention will employ, unless otherwise indicated, conventional techniques of cell biology, molecular biology, cell culture, immunology and the like which are in the skill of one in the art. These techniques are fully disclosed in the current literature. See e.g. Sambrook et al., Molecular Cloning: A Laboratory Manual, $2^{nd}$ Ed., Cold Spring Harbor Laboratory Press, Cold Spring Harbor, N.Y. (1989); Ausubel et al., Current Protocols in Molecular Biology (1987, updated); Brown ed., Essential Molecular Biology, IRL Press (1991); Goeddel ed., Gene Expression Technology, Academic Press (1991); Bothwell et al. eds., Methods for Cloning and Analysis of Eukaryotic Genes, Bartlett Publ. (1990); Wu et al., eds., Recombinant DNA Methodology, Academic Press (1989); Kriegler, Gene Transfer and Expression, Stockton Press (1990); McPherson et al., PCR: A Practical Approach, IRL Press at Oxford University Press (1991); Gait ed., Oligonucleotide Synthesis (1984); Miller & Calos eds., Gene Transfer Vectors for Mammalian Cells (1987); Butler ed., Mammalian Cell Biotechnology (1991); Pollard et al., eds., Animal Cell Culture, Humana Press (1990); Freshney et al., eds., Culture of Animal Cells, Alan R. Liss (1987); Studzinski, ed., Cell Growth and Apoptosis, A Practical Approach, IRL Press at Oxford University Press (1995); Melamed et al., eds., Flow Cytometry and Sorting, Wiley-Liss (1990); Current Protocols in Cytometry, John Wiley & Sons, Inc. (updated); Wirth & Hauser, Genetic Engineering of Animals Cells, in: Biotechnology Vol. 2, Pühler ed., VCH, Weinheim 663-744; the series Methods of Enzymology (Academic Press, Inc.), and Harlow et al., eds., Antibodies: A Laboratory Manual (1987).

The invention relates to a method of improving cell growth of a cell line characterized in that the DHFR activity of said cell line is increased.

In a preferred embodiment of the present invention the method is characterized in that the cell line is a DHFR-deficient or a DHFR-reduced cell line.

In a further embodiment of the present invention the method is characterized in that the gene encoding DHFR and a gene of interest (GOI) encoding the desired product are sequentially introduced into said cell line.

In another embodiment of the present invention the method is characterized in that the DHFR expression cassette is the only mammalian expression unit which is introduced into said cell line during this sequential introduction step.

In another specific embodiment of the present invention the method is characterized in that selection for the gene of interest encoding the desired product is carried out in the absence of methotrexate (MTX).

In a further embodiment of the present invention the method is characterized in that the gene dosage of DHFR is increased.

In a further specific embodiment of the present invention the method is characterized in that the cells of said cell line contain at least 1, preferably at least 3 copies of the DHFR gene.

In a further specific embodiment of the present invention the method is characterized in that the cells of said cell line contain at least 5, at least 10 or at least 25 copies of the DHFR gene.

In another specific embodiment of the present invention the method is characterized in that the expression level of DHFR is increased.

In a further embodiment of the present invention the method is characterized in that the expression level of DHFR is increased at least 2-fold.

In a further embodiment of the present invention the method is characterized in that the expression level of DHFR is increased at least 3-fold, 4-fold, 5-fold, 6-fold, 7-fold, 8-fold, 9-fold, 10-fold, 15-fold or 20-fold.

In a specific embodiment of the present invention the method is characterized in that the DHFR activity is increased by introducing a heterologous DHFR gene, a DHFR minigene, a DHFR mutant or a DHFR encoding sequence from another species as the cell line.

In a further embodiment of the present invention the method is characterized in that said cell line is already transfected with a gene of interest (GOI).

In a further embodiment of the present invention the method is characterized in that said cell line is a mammalian cell line such as a CHO cell line.

In a preferred embodiment of the present invention the method is characterized in that the cell line is CHO-DG44 or CHO-DUKX-B11, preferably CHO-DG44.

In another embodiment of the present invention the method is characterized in that the selection for the gene of interest encoding the desired product is carried out in the presence of hypoxanthine and thymidine (HT) and in the absence of MTX.

In another specific embodiment of the present invention the method is characterized in that DHFR is transfected into the cell line on a separate plasmid than the gene of interest encoding the desired product and whereby DHFR does not serve as selection and/or amplification marker for the gene of interest.

In a further embodiment of the present invention the method is characterized in that the plasmid containing DHFR is transfected sequentially or simultaneously with a plasmid containing the gene of interest.

In a preferred embodiment of the present invention the method is characterized in that the plasmid containing DHFR is transfected sequentially with a plasmid containing the gene of interest.

In another preferred embodiment of the present invention the method is characterized in that said cell line has previously been transfected with a first plasmid containing a gene of interest functionally coupled to a selection marker other than DHFR.

In a further embodiment of the present invention the method is characterized in that said cell line contains heterologous DHFR and at least one other amplification marker such as glutamine synthetase (GS), adenosine deaminase (ADA) or cytosine deaminase (CDA).

In a further specific embodiment of the present invention the method is characterized in that said cell line contains heterologous DHFR and GS.

In another specific embodiment of the present invention the method is characterized in that said cell line contains heterologous DHFR and at least one other selection marker such as puromycin, neomycin or bleomycin.

In a further embodiment of the present invention the method is characterized in that stably transfected cells are selected for by using the selection marker functionally coupled to the gene of interest.

In a further embodiment of the present invention the method is characterized in that stably transfected cells are selected for by using the selection marker functionally coupled to the gene of interest, which is not DHFR.

In a preferred embodiment of the present invention the method is characterized in that the cell density reached by said stably transfected cell line is at least 2-fold higher than that of the corresponding untransfected cell line.

Furthermore, the present invention relates to a method for generating a production host cell line characterized by the following steps
 a. transfecting a host cell with at least one gene of interest encoding a desired product on at least one first plasmid functionally coupled to a selection and/or amplification marker other than DHFR,
 b. Introducing a DHFR expression cassette located on a separate plasmid as in step a,
 c. Selecting for stably transfected cells using the selection marker of step a, whereby the growth characteristics and cell density reached by said cell are better and higher than those of the corresponding untransfected cell line.

Preferably, the present invention relates to a method for generating a production host cell line characterized by the following steps
 a. transfecting a DHFR-deficient or DHFR-reduced host cell with at least one gene of interest encoding a desired product on at least one first plasmid functionally coupled to a selection and/or amplification marker other than DHFR,
 b. Introducing a DHFR expression cassette located on a separate plasmid as in step a,
 c. Selecting for stably transfected cells using the selection marker of step a, whereby the growth characteristics and cell density reached by said cell are better and higher than those of the corresponding untransfected cell line.

In a preferred embodiment of the present invention the method is characterized in that the order of steps a and b is exchanged.

In a preferred embodiment of the present invention the method is characterized in that the order of steps a and b is reversed.

In a preferred embodiment of the present invention the method is characterized in that DHFR is the only mammalian expression unit which is introduced into said cell line during step b.

Furthermore, the present invention relates to host cell obtainable by any one of the described methods.

In a specific embodiment of the present invention the method is characterized in that the cell is a mammalian host cell such as a CHO cell.

In a preferred embodiment of the present invention the method is characterized in that the cell is a CHO-DG44 or CHO-DUKX-B11.

Furthermore, the present invention relates to a method of producing a protein in a cell line, e.g. a mammalian cell line, characterized by the following steps:
(a) Generating a host cell with one of the described methods above containing a gene of interest encoding a protein of interest,
(b) Cultivating the cells, under conditions which allow the proliferation of the cell,
(c) Harvesting the protein of interest e.g. by separating the cells from the supernatant and
(d) Purifying the protein of interest.

Preferably, the present invention relates to a method of producing a protein in a DHFR-deficient or DHFR-reduced cell line, e.g. a mammalian cell line, characterized by the following steps:
(a) Generating a host cell with one of the described methods above containing a gene of interest encoding a protein of interest,
(b) Cultivating the cells, under conditions which allow the proliferation of the cell,
(c) Harvesting the protein of interest e.g. by separating the cells from the supernatant and
(d) Purifying the protein of interest.

In a specific embodiment of the present invention the method is characterized in that the protein of interest is a secreted protein.

In a further embodiment of the present invention the method is characterized in that the cell additionally contains a transgene which encodes an intracellular or a membrane standing protein.

In a preferred embodiment of the present invention the method is characterized in that the transgene is located on the same plasmid as the DHFR expression cassette.

In a further preferred embodiment of the present invention the method is characterized in that the transgene encodes for an anti-apoptotic gene or a transcription factor.

In a specific preferred embodiment of the invention the methods/host cells are characterized in that they are performed/grown in suspension culture.

In a specific preferred embodiment of the invention the methods/host cells are characterized in that they are performed/grown in serum-free culture medium.

The invention generally described above will be more readily understood by reference to the following examples, which are hereby included merely for the purpose of illustration of certain embodiments of the present invention and are not intended to limit the invention in any way.

EXAMPLES

Materials and Methods

Cell Culture

All cell lines used at production and development scale are maintained in serial seedstock cultures in surface-aerated T-flasks (Nunc, Denmark) in incubators (Thermo, Germany) or shake flasks (Nunc, Denmark) at a temperature of 37° C. and in an atmosphere containing 5% $CO_2$.

Seedstock cultures are subcultivated every 2-3 days with seeding densities of 2-3E5 cells/mL. The cell concentration is determined in all cultures by using a hemocytometer. Viability is assessed by the trypan blue exclusion method. All CHO production cells are cultured in BI-proprietary media and their composition may not be revealed.

Fed-Batch Cultivation

Cells are seeded at 3E05 cells/ml into 125 ml shake flasks in 30 ml of BI-proprietary production medium without antibiotics or MTX (Sigma-Aldrich, Germany). The cultures are agitated at 120 rpm in 37° C. and 5% $CO_2$ which is reduced to 2% following day 3. Culture parameters including pH, $pO_2$, $pCO_2$, glucose, lactate and glutamine concentrations are determined daily and pH is adjusted to pH 7.0 using $NaCO_3$ as needed. BI-proprietary feed solution is added every 24 hrs at 30 ml/L*d. Cell densities and viability are determined by trypan-blue exclusion using an automated CEDEX cell quantification system (Innovatis).

Single Cell Sorting

A FACS Vantage (Becton Dickinson) flow cytometer equipped with pulse processing, sort enhancement module, and automatic cell deposition unit is used for analysis and cell sorting. On a dot plot of forward and side scatter (FSC/SSC) a gate is set around single living cells. Sorted cells are deposited into 96-well microtiter plates containing 200 µL growth medium at one cell per well with the automatic cell deposition unit. For sterile sorting the tubing of the cell sorter is cleaned and sterilized by running as sheath fluid for 1 h each of the following solutions: 0.1N NaOH; 0.1% Triton-X-100; 70% ethanol. Subsequently, a sterile sheath tank with PBS is connected to the cell sorter.

RNA Isolation and RT-PCR

RNA from growing cells is isolated using TRIzol® reagent (Invitrogen, Germany) according to the manufacturer's instructions followed by treatment with DNase I for 30 minutes at 37° C. First strand cDNA synthesis is carried out using the Cloned AMV First-Strand cDNA Synthesis Kit (Invitrogen, Germany) starting with 3 µg of total RNA and oligo(dT) oligonucleotides. Quantitative differences in dhfr transcript levels are determined by real-time PCR using the Absolute™ QPCR SYBR® Green Fluorescein Mix (ABgene, Surrey, UK) and a thermal cycler controlled by the MyIQ Real Time Detection software (BioRad, Germany). All experiments are performed in triplicates. DHFR-specific amplificates are generated and quantified relative to tubulin expression levels using the following oligonucleotides: dhfr (sense) SEQ ID NO.1 5'-ATGGTTCGACCGCTGAAC-TGC-3'; dhfr (anti-sense) SEQ ID NO.2 5'-CCACTGAGGAGGTGGTGGT-CATT-3'; tubulin (sense) SEQ ID NO.3 5'-CTCAACGC-CGACCTGCGCAAG-3' and tubulin (anti-sense) SEQ ID NO.4 5'-ACTCGCTGGTGTACCAGTGC-3'.

Example 1

Heterologous DHFR Expression Enhances Cell Growth

DHFR-deficient CHO-DG44 (Urlaub & Chasin, Cell 33, 405-412; 1983) and CHO DUKX-B11 (ATCC CRL-9010) are stably transfected with DNA constructs harbouring the selection markers for puromycin and neomycin, respectively, or and expression plasmid for the DHFR gene. The cells are selected in medium containing the respective antibiotic (puromycin or geneticin) or in selective medium without HT.

The growth characteristics of the arising stable cell pools are than compared in seedstock cultures and during fed-batch cultivation in shake flasks which represent an established down-scale model for fermentation/production processes [Liu C and Hong L; Biochem. Eng. J. (2001) 7:121-125].

Figure 1:
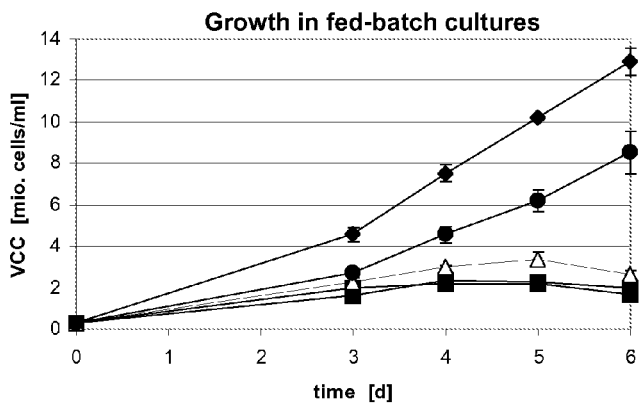
FIG. 1: IMPROVED GROWTH BY HETEROLOGOUS DHFR (a) Cell growth curve in fed-batch processes. Cells were grown in shake-flasks for 5 days and feeded every 24 hours from day 3 on. Viable cell counts were determined daily using the CEDEX system. The following cells were compared: Wild type (WT) CHO cells (-●-; n=4); dhfr-negative DUX-B11 (-Δ-; n=2) and two DG44 cell lines from different sources (-■-; n=4); DG44 cell pools stably transfected with vectors harbouring neomycin (n=6, data not shown) or puromycin (n=6, data not shown) resistance genes or the dhfr gene (-♦-, n=9). A representative growth curve out of five independent experiments is shown.
Figure 1:
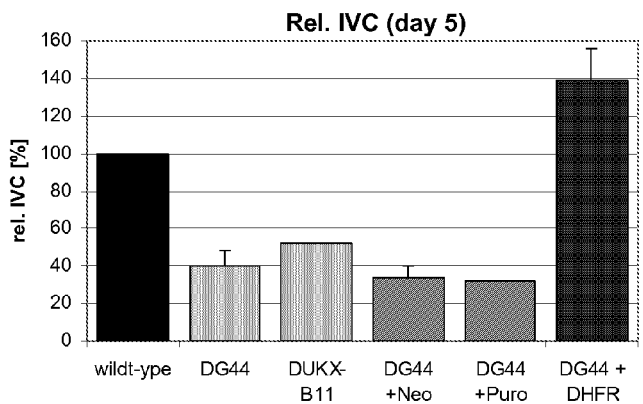
Figure 1:
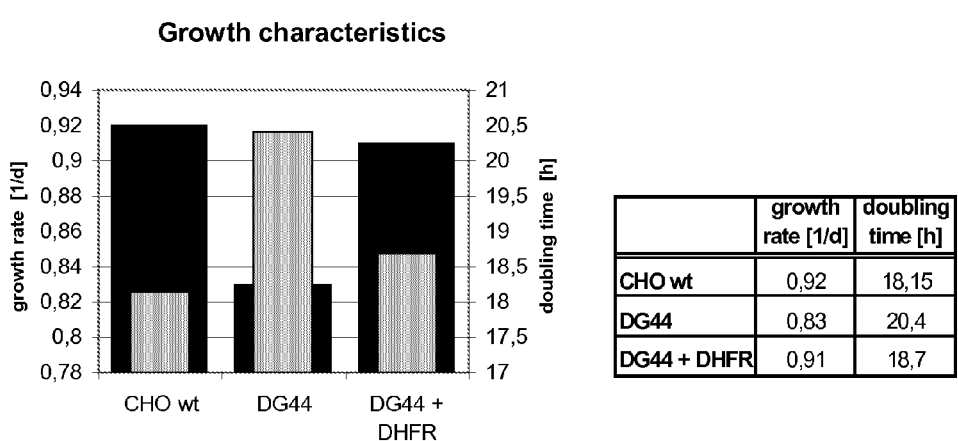

Surprisingly, CHO-deficient DG44 cells show strongly impaired growth compared to parental CHO wild type (wt) cells (FIG. 1). In fed-batch cultures, they grow slower and reach lower maximal cell densities (FIGS. 1a,b), which is in agreement with reduced growth rates measured during seedstock cultivation (FIG. 1c). Interestingly, complementation of DG44 dhfr–/– cells by heterologous DHFR (SEQ ID NOs.5+ 6) expression completely rescues this phenotype. Re-introduction of a DHFR-transgene does not only lead to a reduction in the doubling time, but also the IVC is increased to wild type levels or even beyond. This growth enhancing effect can not only be observed in two different DG44 cell lines, but also applies for CHO DUKX B11 cells transfected with a functional DHFR gene. Transfection with expression constructs harbouring puromycin or neomycin restistance cassettes, however, do not lead to changes in cellular growth characteristics. This indicates, that the growth enhancement is not due to selection and/or cultivation of stable transfectants, but is caused by the re-establishment of functional DHFR expression in dhfr-negative CHO cells.

Example 2

DHFR Enhances Cell Growth in a Dose-Dependent Manner

In order to investigate whether the growth effect mediated by re-introduction of DHFR is dosis dependent, stably DHFR (SEQ ID NOs.5+6) expressing subclones were generated and subjected to FACS-based single-cell cloning to obtain clonal populations with homogenous DHFR expression. Subsequently, the growth properties of these DHFR clones was analysed in fed-batch fermentation runs. As shown in FIG. 2a, DHFR transfected subclones reached far higher IVC levels compared to CHO-DG44 cells, the difference ranging from 2.5 to 6-fold within six days.

To be able to address the question whether elevated IVC levels correlated with enhanced DHFR transcript levels, total RNA was isolated from the DHFR subclones as well as the parental CHO-DG44 cell line and quantitative PCR was performed to analyse DHFR expression (FIG. 2b). In over 80% of the clones analysed, the measured IVCs correlated nicely with the strength of DHFR expression, that means that the clones with the highest DHFR transcript levels exhibited the highest IVCs in the fermentation process. These data suggest that expression of heterologous DHFR in CHO-DG44 cells increases cell growth in a dose-dependent manner.

Reference List

Alt, F. W., Kellems, R. E., Bertino, J. R., and Schimke, R. T. (1978). Selective multiplication of dihydrofolate reductase genes in methotrexate-resistant variants of cultured murine cells. J. Biol. Chem. 253, 1357-1370.

Asselbergs, F. A. and Widmer, R. (1995). Use of the *Escherichia coli* chromosomal DHFR gene as selection marker in mammalian cells. J. Biotechnol. 43, 133-138.

Bailey, J. E., Da Silva, N. A., Peretti, S. W., Seo, J. H., and Srienc, F. (1986). Studies of host-plasmid interactions in recombinant microorganisms. Ann. N.Y. Acad. Sci. 469, 194-211.

Fouser, L. A., Swanberg, S. L., Lin, B. Y., Benedict, M., Kelleher, K., Cumming, D. A., and Riedel, G. E. (1992). High level expression on a chimeric anti-ganglioside GD2 antibody: genomic kappa sequences improve expression in COS and CHO cells. Biotechnology (N.Y.) 10, 1121-1127.

Gu, M. B., Kern, J. A., Todd, P., and Kompala, D. S. (1992). Effect of amplification of dhfr and lac Z genes on growth and beta-galactosidase expression in suspension cultures of recombinant CHO cells. Cytotechnology 9, 237-245.

Kaufman, R. J. (1990). Selection and coamplification of heterologous genes in mammalian cells. Methods Enzymol. 185, 537-566.

Kaufman, R. J. and Sharp, P. A. (1982). Amplification and expression of sequences cotransfected with a modular dihydrofolate reductase complementary dna gene. J. Mol. Biol. 159, 601-621.

Kaufman, R. J., Murtha, P., Ingolia, D. E., Yeung, C. Y., and Kellems, R. E. (1986). Selection and amplification of heterologous genes encoding adenosine deaminase in mammalian cells. Proc. Natl. Acad. Sci. U.S.A 83, 3136-3140.

Page, M. J. and Sydenham, M. A. (1991). High level expression of the humanized monoclonal antibody Campath-1H in Chinese hamster ovary cells. Biotechnology (N.Y.) 9, 64-68.

Pallavicini, M. G., Deteresa, P. S., Rosette, C., Gray, J. W., and Wurm, F. M. (1990). Effects of methotrexate on transfected DNA stability in mammalian cells. Mol. Cell Biol. 10, 401-404.

Pendse, G. J., Karkare, S., and Bailey, J. E. (1992). Effect of cloned gene dosage on cell growth and hepatitis B surface antigen synthesis and secretion in recombinant CHO cells. Biotechnology and Bioengineering 40, 119-129.

Puck, T. T. (1957). The genetics of somatic mammalian cells. Adv. Biol. Med. Phys. 5, 75-101.

Schimke, R. T., Kaufman, R. J., Alt, F. W., and Kellems, R. F. (1978). Gene amplification and drug resistance in cultured murine cells. Science 202, 1051-1055.

Simonsen, C. C. and Levinson, A. D. (1983). Isolation and expression of an altered mouse dihydrofolate reductase cDNA. Proc. Natl. Acad. Sci. U.S.A 80, 2495-2499.

Snapka, R. M., Ge, S., Trask, J., and Robertson, F. (1997). Unbalanced growth in mouse cells with amplified dhfr genes. Cell Prolif. 30, 385-399.

Urlaub, G. and Chasin, L. A. (1980). Isolation of Chinese hamster cell mutants deficient in dihydrofolate reductase activity. Proc. Natl. Acad. Sci. U.S.A 77, 4216-4220.

Urlaub, G., Kas, E., Carothers, A. M., and Chasin, L. A. (1983). Deletion of the diploid dihydrofolate reductase locus from cultured mammalian cells. Cell 33, 405-412.

Werner, R. G. (2004). Economic aspects of commercial manufacture of biopharmaceuticals. J. Biotechnol. 113, 171-182.

Wurm, F. M. and Jordan, M. (2003). Gene Transfer and Gene Amplification in Mammalian Cells. In: Gene Transfer and Expression in Mammalian Cells, ed. S. C. Makrides Elsevier Science B.V., 309-335.

The invention claimed is:

1. A method for generating a production host cell line characterized by the following steps a) transfecting a DHFR-deficient or DHFR-reduced host cell with at least one gene of interest encoding a desired product on at least one first plasmid functionally coupled to a selection and/or amplification marker other than DHFR, b) Introducing a DHFR expression cassette located on a separate plasmid from the plasmid in step a, c) Selecting for stably transfected cells using the selection marker of step a, wherein said DHFR does not serve as a selection and/or amplification marker, whereby the growth characteristics and cell density reached by said cell are better and higher than those of the corresponding untransfected cell line, wherein the said host cell line is a CHO cell line.

2. A method according to claim 1 whereby the order of steps a and b is exchanged.

3. A method according to claim 1 whereby DHFR is the only mammalian expression unit which is introduced into said cell line during step b.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: dhfr (sense)

<400> SEQUENCE: 1
atggttcgac cgctgaactg c                                          21

<210> SEQ ID NO 2
<211> LENGTH: 23
<212> TYPE: DNA
<213> ORGANISM: Artificial
<220> FEATURE:
<223> OTHER INFORMATION: dhfr (anti-sense)

<400> SEQUENCE: 2
ccactgagga ggtggtggtc att                                        23

<210> SEQ ID NO 3
<211> LENGTH: 21
<212> TYPE: DNA
<213> ORGANISM: Artificial
<220> FEATURE:
<223> OTHER INFORMATION: tubulin (sense)

<400> SEQUENCE: 3
ctcaacgccg acctgcgcaa g                                          21

<210> SEQ ID NO 4
<211> LENGTH: 20
<212> TYPE: DNA
<213> ORGANISM: Artificial
<220> FEATURE:
<223> OTHER INFORMATION: tubulin (anti-sense)

<400> SEQUENCE: 4
actcgctggt gtaccagtgc                                            20

<210> SEQ ID NO 5
<211> LENGTH: 798
<212> TYPE: DNA
<213> ORGANISM: Cricetulus sp.

<400> SEQUENCE: 5
```

-continued

```
aatttcgcgc caaacttggg ggaagcacag cgtacaggct gcctaggtga tcgctgctgc    60
tgtcatggtt cgaccgctga actgcatcgt cgccgtgtcc cagaatatgg gcatcggcaa   120
gaacggagac cttccctggc caatgctcag gaacgaattc aagtacttcc aaagaatgac   180
caccacctcc tcagtggaag gtaaacagaa cttggtgatt atgggccgga aaacctggtt   240
ctccattcct gagaagaatc gacctttaaa ggacagaatt aatatagttc tcagtagaga   300
gctcaaggaa ccaccacaag gagctcattt tcttgccaaa agtctggacg atgccttaaa   360
acttattgaa caaccagagt tagcagataa agtggacatg gtttggatag ttggaggcag   420
ttccgtttac aaggaagcca tgaatcagcc aggccatctc agactctttg tgacaaggat   480
catgcaggaa tttgaaagtg acacgttctt cccagaaatt gatttggaga aatataaact   540
tctcccagag tacccagggg tccttctga agtccaggag gaaaaaggca tcaagtataa    600
atttgaagtc tatgagaaga aaggctaaca gaaagatact tgctgattga cttcaagttc   660
tactgctttc ctcctaaaat tatgcatttt tacaagacca tgggacttgt gttggcttta   720
gatctatgag ttattctttc tttagagagg gatagttagg aagatgtatt tgttttgtgg   780
taccagagat ggaacctg                                                 798

<210> SEQ ID NO 6
<211> LENGTH: 1047
<212> TYPE: DNA
<213> ORGANISM: Mus musculus

<400> SEQUENCE: 6 ggggcgggc cttagctgcg caagtggtac acagctcagg gctgcgattt cgcgccaaac    60
ttcacggcaa tcctagcgtg aaggctggta ggatttatc cccgctgcca tcatggttcg   120
accattgaac tgcatcgtcg ccgtgtccca aaatatgggg attggcaaga acggagaccg   180
accctggcct ccgctcagga acgagttcaa gtacttccaa agaatgacca caacctcttc   240
agtggaaggt aaacagaatc tggtgattat gggtaggaaa acctggttct ccattcctga   300
gaagaatcga cctttaaagg acagaattaa tatagttctc agtagagaac tcaaagaacc   360
accacgagga gctcattttc ttgccaaaag tttggatgat gccttaagac ttattgaaca   420
accggaattg gcaagtaaag tagacatggt ttggatagtc ggaggcagtt ctgtttacca   480
ggaagccatg aatcaaccag gccacctcag actctttgtg acaaggatca tgcaggaatt   540
tgaaagtgac acgttttttcc cagaaattga tttggggaaa tataaacttc tcccagaata   600
cccaggcgtc ctctctgagg tccaggagga aaaaggcatc aagtataagt ttgaagtcta   660
cgagaagaaa gactaacagg aagatgcttt caagttctct gctcccctcc taaagctatg   720 cattttata agaccatggg acttttgctg gctttagatc tatgagtaat tatttcttta   780
gggaggggta gttggaagaa ttgtttgttt tgtgatcttg gggatggaac ctaagaccca   840
gtgcgtgctg agcaaatgct atactgctga gccaccccaa ccctagcccc tatataattc   900
taaacaatat gttgtcattt cccagtaatc taacaaggta tagtaaaagt gccttaagaa   960
atgtcacttg ctataaaggt ctcagtgccc ctcccatgag acctcaagtc ccccccccc   1020 cccccccc ccccccccc ccccccc                                        1047
```